(12) United States Patent
Reinhardt et al.

(10) Patent No.: US 6,315,781 B1
(45) Date of Patent: Nov. 13, 2001

(54) DEVICE AND METHOD FOR EXTRACTING AN OBJECT FEATURING A LONGITUDINAL INNER LUMEN FROM ITS ANCHORING IN A BODY

(75) Inventors: Jörg Reinhardt; Siegfried Schreiber, both of Grenzach-Wyhlen (DE)

(73) Assignee: Vascomed Institute Für Kathetertechnologie GmbH (DE)

( * ) Notice: Subject to any disclaimer, the term of this patent is extended or adjusted under 35 U.S.C. 154(b) by 0 days.

(21) Appl. No.: 09/367,942

(22) PCT Filed: Oct. 5, 1998

(86) PCT No.: PCT/DE98/02976

§ 371 Date: Aug. 20, 1999

§ 102(e) Date: Aug. 20, 1999

(87) PCT Pub. No.: WO99/22807

PCT Pub. Date: May 14, 1999

(30) Foreign Application Priority Data

Nov. 3, 1997 (DE) ................................. 197 48 455

(51) Int. Cl.[7] .................................................. A61B 17/50
(52) U.S. Cl. ........................................... 606/108; 607/126
(58) Field of Search ..................... 607/116, 122, 607/126–128; 606/108–129; 600/373, 374, 375, 377

(56) References Cited

U.S. PATENT DOCUMENTS

| 4,574,800 | * | 3/1986 | Peers-Trevarton | 606/1 |
| 4,576,162 | * | 3/1986 | McCorkle | 606/159 |
| 5,242,430 | * | 9/1993 | Arenas et al. | 604/194 |
| 5,620,451 | | 4/1997 | Rosborough . | |
| 5,632,749 | | 5/1997 | Goode et al. . | |
| 6,136,005 | * | 10/2000 | Goode et al. | 606/108 |

FOREIGN PATENT DOCUMENTS

| 0573334 | 5/1993 | (EP) . |
| 91/19532 | 12/1991 | (WO) . |
| 97/17021 | 5/1997 | (WO) . |

* cited by examiner

*Primary Examiner*—Kennedy Schaetzle
(74) *Attorney, Agent, or Firm*—Baker & Daniels

(57) ABSTRACT

A device permitting simple and reliable extraction of an object with a longitudinal inner lumen from its anchoring in a body, e.g. a cardiac pacemaker cable having an electrode cable with a spiral coil, has an actuation device (20) and an anchoring part (4). By turning an actuation sleeve (22) of the actuation device (20), a tractive force is applied to a cable (8) resting in a tube (11) in such a way that it can be moved in its longitudinal direction. On the distal end of the cable (8), there is a tiltable anchoring part (4, 5) with a cross section in the form of a parallelogram. Once the contact surface (12) on the distal end of the tube (11) comes in contact with the stop surface (7) of the anchoring part (4) running at an angle thereto, a tilting moment can be applied to the anchoring part (4) by continuing to pull on the cable (8), as a result of which the cable (8) bends and the anchoring part (4) turns sideways in the inner lumen of the spiral coil of an electrode cable, thereby engaging in the spiral coil so that pulling the actuation device (20) permits producing an extraction force on the spiral coil of the cardiac pacemaker electrode.

16 Claims, 4 Drawing Sheets

DEVICE AND METHOD FOR EXTRACTING AN OBJECT FEATURING A LONGITUDINAL INNER LUMEN FROM ITS ANCHORING IN A BODY

TECHNICAL FIELD

The invention refers to a device for extracting an object featuring a longitudinal inner lumen from its anchoring in a body, in particular a cardiac pacemaker cable having an electrode cable with a spiral coil, with the device having a tube through which a cable extends which, on its distal end projecting from the tube, has an anchoring part which can be inserted into the inner lumen of the object together with the tube, where such anchoring part can be activated through a relative motion between the tube and the cable by means of an actuation device.

BACKGROUND ART

Such a device for extracting a cardiac pacemaker electrode which has grown onto the heart by means of cardiac pacemaker electrode cable with a spiral coil is known from the international patent application WO 91/19532 A1 and has an anchoring part in the form of a split tube segment connected to the distal end of the cable and whose ends facing the tube have been slightly pre-spread towards the outside. By pulling on the cable, the pre-spread, split tube segment is activated, the tube segment halves are spread apart and their free ends engage in the inner side of the spiral coil of the electrode cable.

In a device of this type, depending on the diameter of the inner lumen of the electrode cable, different sizes must be provided for the anchoring part of the extraction device. Another disadvantage is that in case the diameter of the inner lumen is too large, the tube segment halves can fold, as a result of which safe anchoring is no longer ensured.

In addition, such an extraction device only works reliably with multiple-coil electrodes, in particular four-coil electrodes.

U.S. Pat. No. 5,632,749 also describes a device of above type in which the anchoring part is a split sleeve which can be activated by means of a relative motion between the tube and the cable. The sleeve is split along its longitudinal axis and designed in such a way that its diameter can be enlarged for the purpose of activating the device. For that purpose, on the distal end of the tube as well as on the distal end of the cable, conical surfaces facing each other are provided which can be engaged by pulling the cable, causing the split sleeve to enlarge and press against the spiral coil of the electrode cable along a large number of coils in order to achieve traction. Such a type of device has the disadvantage that sufficient traction requires large axial forces on the split sleeve by pulling the cable and holding against it with the tube. Another disadvantage is that only a relatively small enlargement of the diameter of the split sleeve is possible, as a result of which, depending on the diameter of the inner lumen of the spiral coil of the cardiac pacemaker cable, different sizes of extracting devices must be available.

DISCLOSURE OF INVENTION

Based on the state of the art described above, the object of the invention is to produce an extraction device, in particular an extraction device for single-coil or multiple-coil cardiac pacemaker electrodes, which can be used reliably and largely independent of the diameter of the inner lumen and which makes it possible to transmit large extraction forces.

In a device of the type identified above, this task is solved by providing the tube with a contact surface on its distal end and the anchoring part with a stop surface on its side facing the tube, with the contact surface and the stop surface forming an acute angle with each other in such a way that the anchoring part can be tilted towards the anchoring in the inner lumen of the object with respect to the longitudinal axis of the tube, in case the contact surface and the stop surface engage under force.

In a preferred embodiment, the anchoring part comprises a tube segment whose outside diameter corresponds to the outside diameter of the tube and which has been produced by simply cutting off tube segments at an angle. In such a tube segment, which has the shape of a parallelogram in its longitudinal cross section, a tilting moment is produced in a simple manner through the pulling force on the cable and transferred to the anchoring part, as a result of which, after bending the cable and tilting it in top view towards the longitudinal axis of the tube, the outline of the anchoring part are enlarged, which allows it to reliably engage the spiral coil of an electrode cable.

It is obvious that in lieu of a tube segment with one or two ends having been cut off at an angle, anchoring parts of a different shape can be used; it is only important that such anchoring parts are shaped in such a way that they permit, after bending of the cable and tilting the anchoring part, traction or lockup with the interior wall of a cavity of the object to be extracted.

In a preferred embodiment, the stop contact of the anchoring extends at an angle to the longitudinal axis of the tube part prior to its activation, whereas the contact surface of the tube is perpendicular to the longitudinal axis of the tube.

Such an arrangement has the advantage of simple producibility and reliable transmission of large forces.

The distal end face of the tube segment can run transversally to the longitudinal axis of the tube segment or at an angle to the longitudinal axis of the tube segment. Preferably, the end face and the stop surface run parallel to each other. To achieve proper cable guiding, the cable has an outside diameter which is roughly equivalent to that of the interior diameter of the tube segment and of the tube. Preferably, the cable is only fastened on the distal end of the anchoring part, as a result of which the anchoring part can easily be tilted by bending the cable, and no large forces are required for tilting and radial displacement. It is advisable that prior to tilting of the anchoring part, the stop surface and the longitudinal axis of the tube and the cable form an angle between 15 and 75 degrees. In this case, the contact surface of the tube may also be at an angle of less than 90 degrees with respect to the longitudinal axis of the tube.

The actuation device has a threaded bolt connected to the cable; such threaded bolt has an actuation sleeve with an internal thread which can be pulled to create a force against a handle sleeve in which the proximal end of the tube has been fastened. Instead of using a threaded assembly, however, it is also possible to create the tractive force directly with a sleeve which can be locked in a retreated position, e.g. by a bayonet-like connection.

Below, this present invention is explained in detail in a reference example shown in the drawing.

BEST MODE FOR CARRYING OUT THE INVENTION

Figure 1:
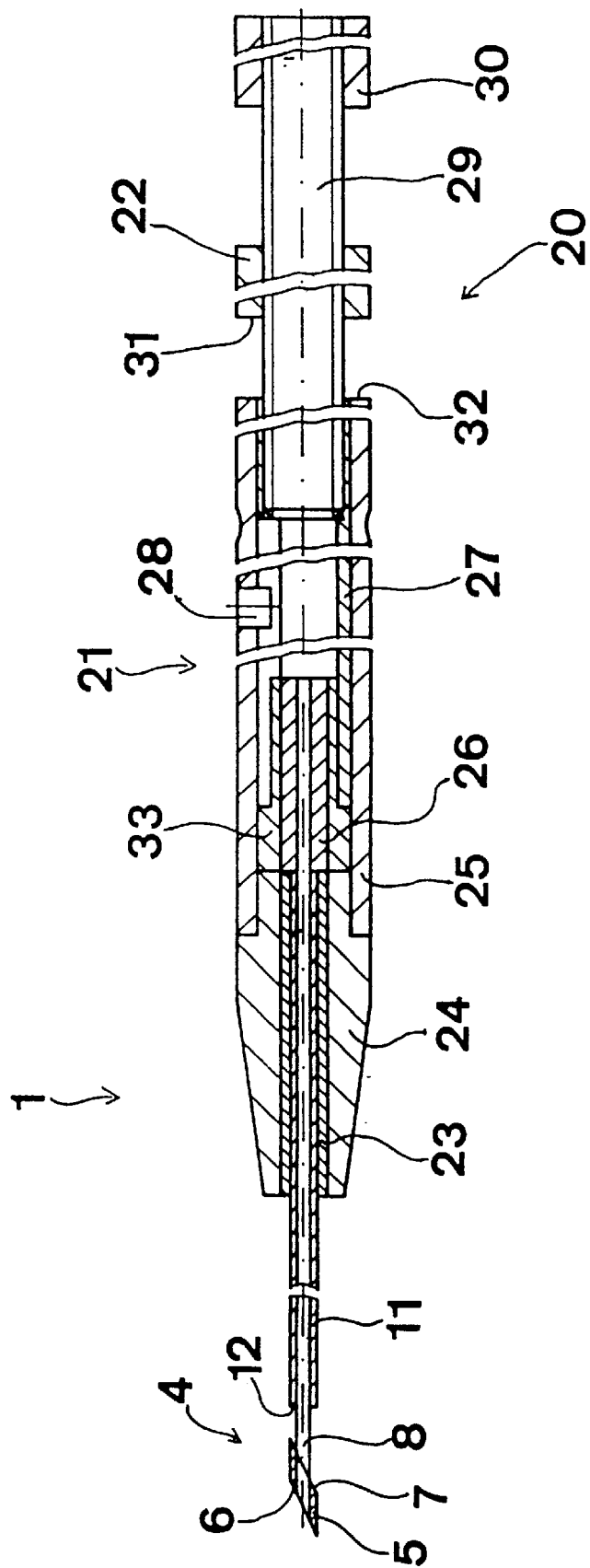
FIG. 1 shows an embodiment of the invention in the form of a device for extracting transvenously implanted cardiac pacemaker electrodes in a longitudinal cross section.

The device for extracting an object having a longitudinal inner lumen from its anchoring in a body depicted in FIG. 1 is an extraction device 1 for removing transvenously implanted cardiac pacemaker electrodes whose distal end[s] have been anchored in a patient's heart muscle. Such cardiac pacemaker electrodes are connected to their corresponding cardiac pacemaker by means of an electrode cable.

Figure 2:
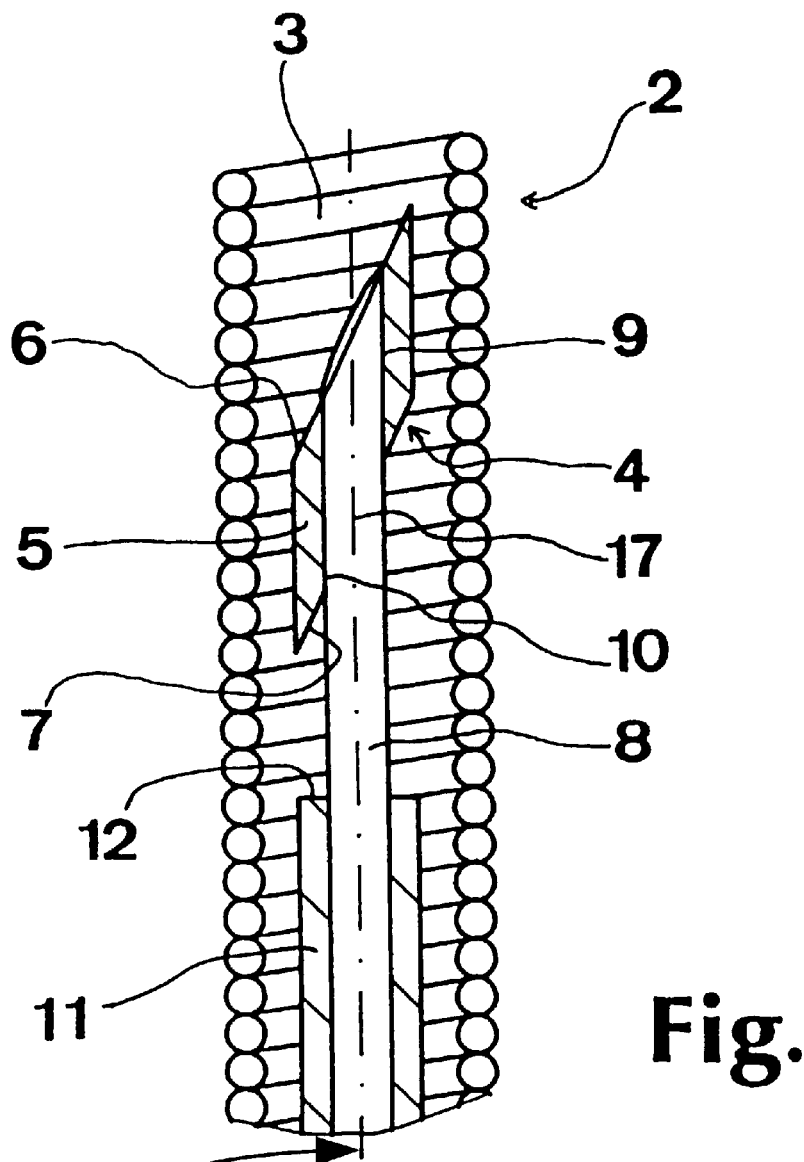
FIG. 2 depicts the anchoring part and the front end of the tube of the device in the inner lumen of the spiral coil of a cardiac pacemaker electrode cable in a longitudinal section (enlarged view compared to FIG. 1)

FIG. 2 shows a section of a spiral coil 2 of a cardiac pacemaker electrode cable surrounded by an insulating jacket, not depicted in the drawing, and which is located in the immediate proximity of the cardiac pacemaker electrode, not depicted in the drawing, which is connected to a spiral coil 2 consisting of conductive and elastic metal so that it conducts electricity.

The spiral coil 2, which is connected with the electrode—not depicted in the drawing—in the top part of FIG. 2, has an inner lumen 3 whose diameter can range from 0.5 to 1.2 mm FIG. 2 shows the front end of the extraction device shown in FIG. 1 where such extraction device has been inserted into the spiral coil of the cardiac pacemaker electrode cable so that, once a tractive force is applied to the section of the spiral coil 2 adjacent to the cardiac pacemaker electrode, the cardiac pacemaker electrode can be extracted from the heart muscle tissue.

In the embodiment shown in the drawing, the anchoring part 4 comprises a tube segment 5 whose ends have been cut off at an angle. As a result, the tube segment 5 has a face end 6 running at an angle to its longitudinal axis 40 on its distal end, and on its proximal end a stop surface 7 which also runs at an angle thereto. As shown in FIGS. 1 and 2, the face end 6 and the stop surface 7 may be parallel to each other, as a result of which a large number of tube segments 5 can be manufactured in a simple manner by cutting a tube at an angle.

With respect to the longitudinal axis 40 of the tube segment 5 which is also the longitudinal axis of the tube 11, the face end 6 and the stop surface 7 form an angle which is preferably between 15 and 75 degrees.

The anchoring part 4 designed as a tube segment 5 with end faces running at an angle to each other is connected with a cable 8, as shown in FIGS. 1 and 2. They are connected with each other in the proximity of the face end 6, e.g. by laser welding, gluing, crimping, soldering or by means of memory effects.

Starting on the face end 6 in axial direction, the connection only runs as far as the cable 8 is covered by the tube segment 5 along its entire circumference. As a result thereof, the cable 8 can be moved radially in its non-connected area 10 since the angle of the stop area 7 creates a lateral recession in the tube segment 5.

As also shown in FIGS. 1 and 2, the cable 8 projects on the distal end of the tube 11, with the distal end of the tube 11 forming a contact surface 12 which, in the described embodiment, runs perpendicular to the longitudinal axis of the tube 11.

The tube 11 has an outside diameter of less than 1 millimeter, e.g. between 0.4 and 0.8 millimeter. The cable 8 has a diameter of less than 0.5, e.g. 0.2 millimeter, and rests inside of the tube 11 in such a way that it can slide without problems.

Figure 3:
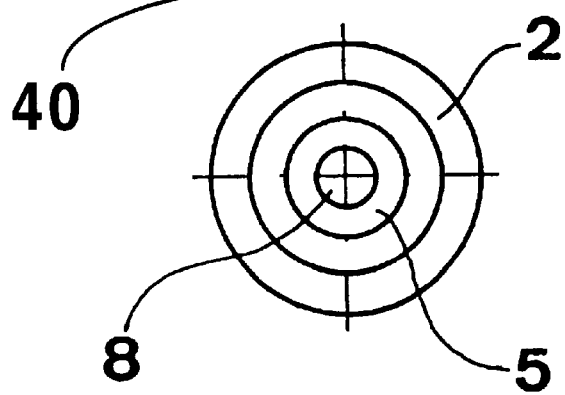
FIG. 3 represents a top view of the arrangement shown in FIG. 2, depicting its end shown on the top in FIG. 2.

The view shown in FIG. 3 illustrates the concentric arrangement of the tube segment 5, the cable 8 and the spiral coil 2 prior to anchoring of the tube segment 5 in the spiral coil 2.

When the cable 8 is pulled into the tube 11 from its insertion position shown in FIGS. 1 and 2, the stop surface 7 of the tube segment 5 ultimately comes in contact with the contact surface 12 at the distal end of the tube 11. Further pulling the cable 8 into the tube 11 produces a tilting moment by means of which the tube segment 5 is tilted as shown in FIG. 4 and engages with its distal edge area 13 as well its proximal edge area 14 into the spiral coil 2 and, as a result of such tilting, creates an area of engagement 15, 16 in the spiral coil 2 in its edge areas 13 and 14.

Figure 4:
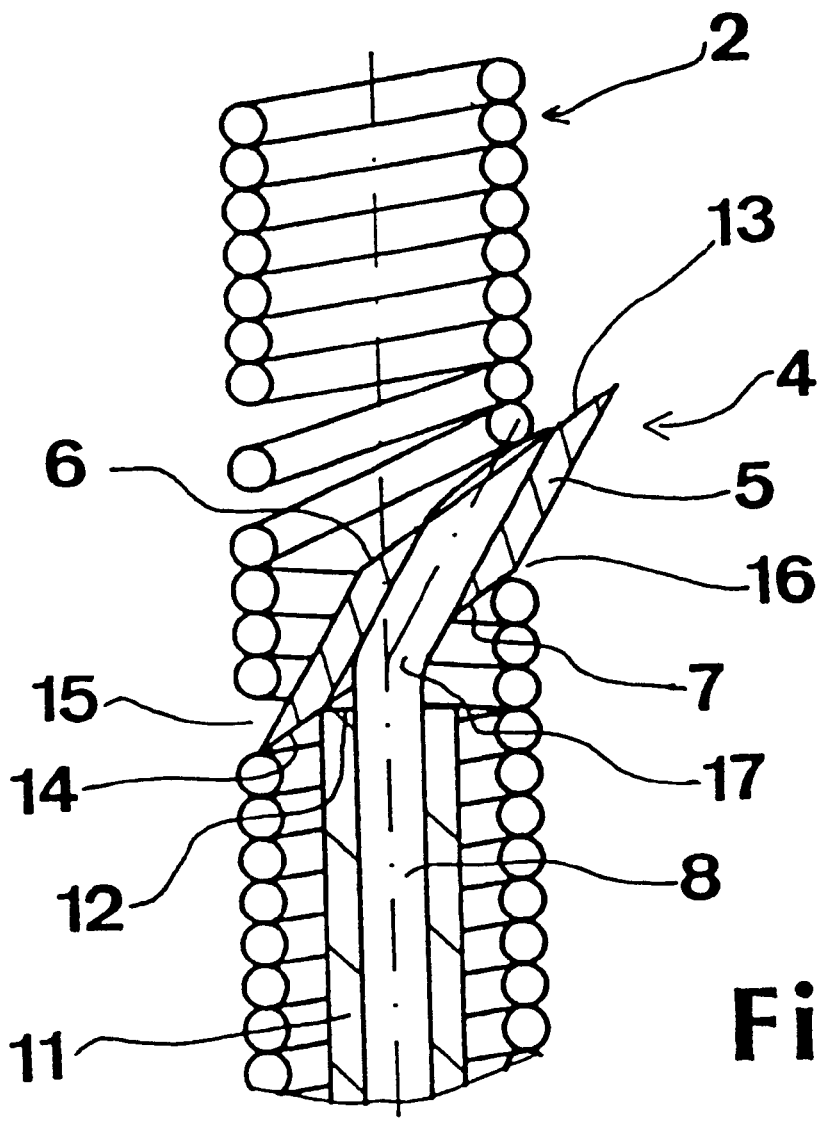
FIG. 4 is a representation corresponding to that of FIG. 2 where the anchoring part has already partly engaged in the spiral coil.

As depicted in FIG. 4, tilting of the tube segment 5 leads to bending of the cable 8 in its bending area 17. The bending area 17 largely corresponds to the non-connected area 10 since in the bending area 17, the cable 8 is not enclosed on all sides by the tube segment 5. Because of the lateral opening caused by the angular orientation of the stop surface 7, the cable can deflect radially as soon as, by pressing together the tube segment 5 and the tube 11, a tilting moment is applied to the anchoring part 4 in the form of a tube segment 5. The tilting moment is created since the contact surface 12 and the stop surface 7 do not run parallel to each other.

It will be obvious to those skilled in the art that the specific geometry of the embodiment described herein is only one of many possibilities to design an anchoring part 4 which, once a cable 8 is pulled, tilts with respect to the longitudinal axis of the tube 11 through which the cable extends, leading to a change in contours.

Figure 5:
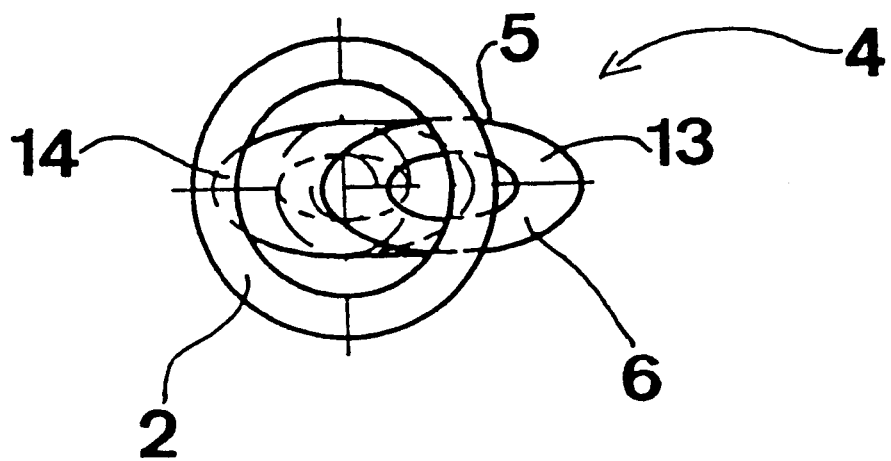
FIG. 5 is a top view as shown in FIG. 3.

A comparison of FIGS. 3 and 5 shows that tilting the anchoring part 4 shown in top view designed as a tube segment 5 along the longitudinal axis of the spiral coil 2 causes a change in contours where the originally circular outline of the tube segment 5 changes to two ellipses located adjacent to each other as shown in FIG. 5. Since tilting leads to a widening of the anchoring part 4, engagement of the anchoring part 4 in the form of a tube segment 5 is achieved in a simple manner without requiring complicatedly shaped, movable parts. The only requirements are that the cable 8 can be bent by the tilting forces and that a relative motion between the stop surface 7 and the contact surface 12 produces a tilting moment by means of which the anchoring part 4 can be tilted to widen its contours in top view.

Figures 6, 7:
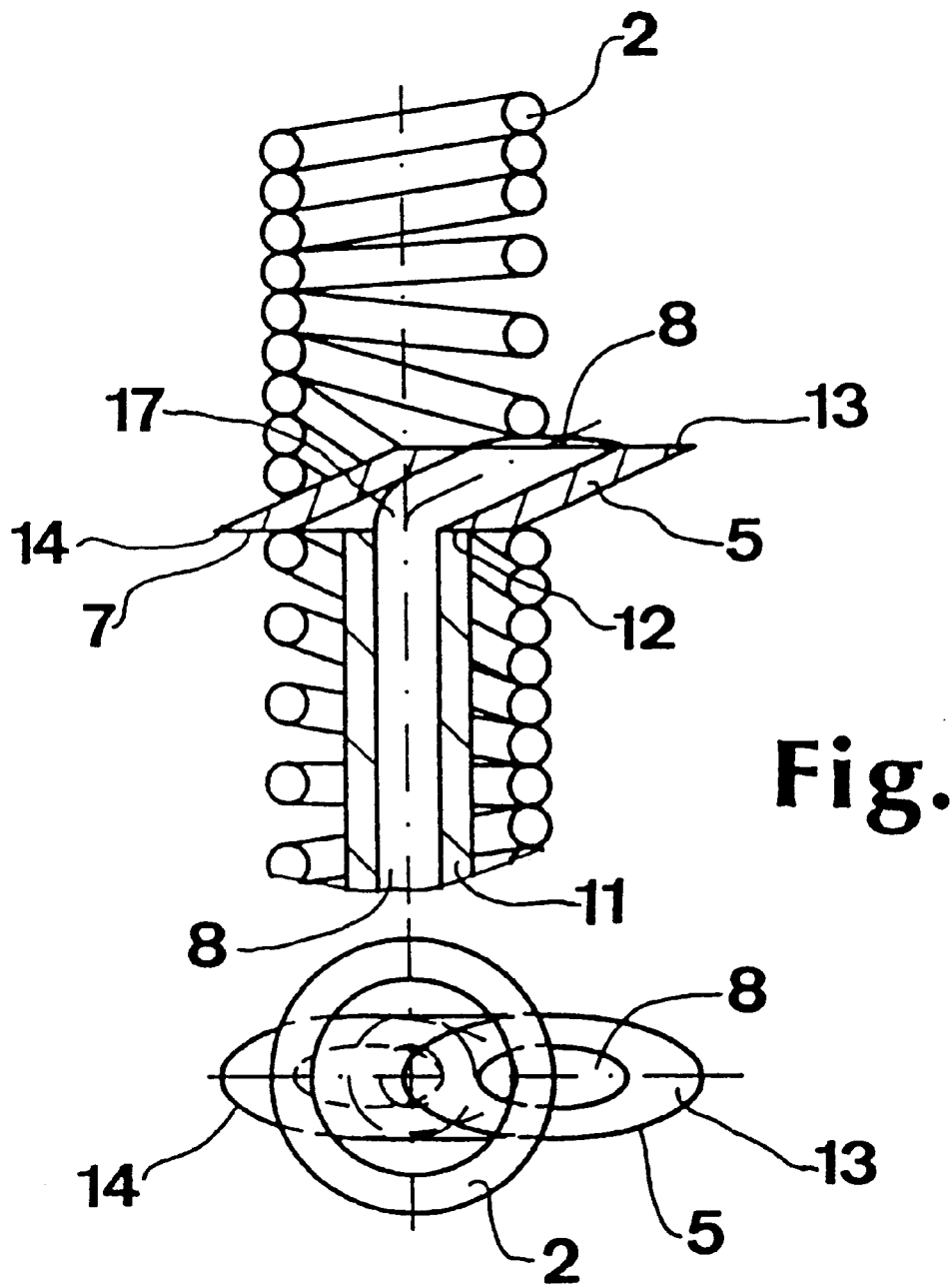
FIG. 6 is a representation corresponding to that of FIGS. 2 and 4 where the anchoring part has engaged in its final position.
FIG. 7 is a representation corresponding to that of FIGS. 3 and 5 with a top view of the end of the spiral coil shown in the top part of FIG. 6.

The position of the tube segment 5 depicted in FIGS. 4 and 5 can be changed by further pulling the cable 8 and bending the cable 8 in the bending area 17 up to a position with maximal deflection shown in FIG. 6. FIG. 6 shows the intended engagement position with maximum deflection width of the tube segment 5. In this final position, the stop surface 7 and the contact surface 12 are parallel to each other. The distal edge areas 13 and 14 of the tube segment 5 extend through the spiral coil 2 up to a point where good lockup and therefore good transmission of force is ensured.

In case it is impossible to extract the cardiac pacemaker electrode having a spiral coil 2 by pulling on the extraction device 1, the extraction device 1 can simply be disengaged from the spiral coil 2 by screwing the assembly consisting of the tube segment 5, the cable 8 and the tube 11 off the spiral coil 2 by manual or motor-powered rotation in the direction of its distal end. The fact that the extraction device 1 described does not allow the user to undo tilting of the anchoring part in the form of a tube segment 5 to reset it to the original position shown in FIG. 2 is therefore no disadvantage in the case of extractions of cardiac pacemaker electrode cables with spiral coils.

In addition to the anchoring part 4, the cable 8 and the tube 11, FIG. 1 also shows an embodiment of an assembly for applying the tractive force on the cable 8 that is required to tilt the anchoring part 4. The actuation device 20 provided for that purpose comprises a handle 21 to receive the tube 11 and an actuation sleeve 22 making it possible to convert a rotation with a rotary power into a tractive force on the cable 8 by means of a thread assembly to activate and anchor the anchoring part 4 after insertion into the distal end of the spiral coil 2 of the cardiac pacemaker electrode cable.

The tube 11 extends through a tube fastening sleeve 23 which, in turn, is fastened in a handle head. The handle head 24 is fastened at the proximal end of a handle sleeve 25. The cable 8 runs through the tube fastening sleeve 23 fastened onto the handle head 24 to a cable fastening sleeve 26 which has been permanently fastened to the proximal end of the cable 8 and, in turn, has been fastened to a connection part 33.

The connection part 33 can be moved axially inside of the handle sleeve 25 and has been permanently fastened on the first end of an axially movable connection sleeve 27. The connection sleeve 27 can be moved axially in the handle sleeve 25. As a rotation lock, the connection sleeve 27 has a longitudinal slot into which a bolt 28 projects.

On its second end, the connection sleeve 27 movable in longitudinal direction is connected to a thread bolt 29 projecting from the handle sleeve 25 of the 21 handle 21. On its proximal end, the thread bolt 29 has a connection element 30. The connection element 30 can be provided with a transverse bore for a traction cable and/or a recession for a locating ball of a rotation drive to rotate the entire assembly depicted in FIG. 1, as already explained in the context of FIG. 6.

By turning the connection sleeve 27 having an interior thread on the thread bolt 29, the end face 31 of the actuation sleeve 22 can be pulled against the end face 32 of the handle sleeve 25 to apply a carefully controlled tractive force on the thread bolt 29, the connection sleeve 27, the connection piece 33, the cable fastening sleeve 26 and therefore the cable 8.

To activate the extraction device 1 shown in FIG. 1, it is therefore only necessary, once such extraction device has been inserted into the spiral coil 2, to engage the actuation sleeve 22 by turning it against the handle sleeve 25 and to continue turning to tilt the anchoring part 4. The wide range of deflection width, depicted particularly well in FIG. 7, results in very reliable anchoring which also permits the transmission of large forces in spiral coils with a very broad range of diameters.

What is claimed is:

1. A device for extracting an object featuring a longitudinal inner lumen from its attachment in a body, wherein said extracting device comprises:

a tube having a longitudinal axis, a distal end, and a proximal end, said distal end having a contact surface;

a cable extending through said tube, said cable having a distal end which projects from said distal end of said tube, said distal end having an anchoring part with a stop surface facing said contact surface of said tube, said stop surface and said contact surface defining an acute angle from about 15 degrees to about 75 degrees, one of said stop surface and said contact surface disposed at an acute angle to said longitudinal axis, wherein said anchoring part, together with said tube, can be inserted into the inner lumen of the object to be extracted; and an actuation device for activating relative motion between said tube and said cable such that, when said stop surface of said anchoring part is drawn towards said contact surface of said tube distal end, said anchoring part tilts with respect to the longitudinal axis of said tube as said contact surface and said stop surface are drawn together and causing said anchoring part to engage said inner lumen, thereby anchoring said anchoring part in said inner lumen of the object to be extracted.

2. A device according to claim 1, wherein:

said anchoring part is a tube segment.

3. A device according claims 2, wherein:

said cable has an outside diameter which is roughly equivalent to the inside diameter of said tube segment and the inside diameter of said tube.

4. A device according to claim 1, wherein:

said anchoring part and said tube have the same outside diameter.

5. A device according to claim 1, wherein:

said contact surface of said tube is substantially perpendicular to the longitudinal axis of the tube.

6. A device according to claim 1, wherein:

said anchoring part is tube segment having proximal and distal end faces, said stop surface being located on said proximal end face, where said distal end face is parallel to said stop surface.

7. A device according to claim 1, wherein;

said cable is fastened to said distal end of said anchoring part.

8. A device according to claim 1, wherein said actuation device further comprises:

a thread bolt permanently connected to said cable in such a way that they can not rotate with respect to each other, said thread bolt having an actuation sleeve;

a handle sleeve in which the proximal end of the tube has been fastened; and said actuation sleeve of said thread bolt can be pulled against said handle sleeve to produce a tractive force on said cable.

9. A method for extracting an object featuring a longitudinal inner lumen from its attachment in a body, comprising the steps of:

A) providing an extracting device comprising a tube having a longitudinal axis, a distal end, said tube distal end having a contact surface, a cable extending through said tube, said cable having a distal end which projects from said tube, said cable distal end having an anchoring part with a stop surface facing said contact surface of said tube, said stop surface and said contact surface defining an acute angle from about 15 degrees to about 75 degrees, one of said stop surface and said contact surface disposed at an acute angle to said longitudinal axis, an actuation device for activating relative motion between said tube and said cable such that said stop surface of said cable is drawn toward said contact surface of said tube distal end;

B) inserting said anchoring part and said tube into said inner lumen of said object to be extracted;

C) activating said actuation device so that said stop surface is drawn toward said contact surface, so that said anchoring part tilts with respect to the longitudinal axis of said tube as said contact surface and said stop surface are drawn together; causing said anchoring part to engage said inner lumen, thereby anchoring said anchoring part in said inner lumen of the object to be extracted; and D) withdrawing said extracting device and said object to be extracted from the body.

10. The method of claim 9, wherein:

said anchoring part of said extracting device in step A is a tube segment.

11. The method of claim 10, wherein:

said cable of the extracting device of step A has an outside diameter which is roughly equivalent to the inside diameter of said tube segment and the inside diameter of said tube.

12. The method of claim 9, wherein:

said anchoring part and said tube of said extracting device in step A have the same outside diameter.

13. The method of claim 9, wherein:

said anchoring part is a tube segment having proximal and distal end faces, said stop surface being located on said proximal end face, where said distal end face is parallel to said stop surface.

14. The method of claim 9, wherein:

said cable of said extracting device in step A is fastened to said distal end of said anchoring part.

15. The method of claim 9, wherein:

said contact surface of said tube is substantially perpendicular to the longitudinal axis of the tube.

16. The method of claim 9, wherein said actuation device further comprises:

a thread bolt permanently connected to said cable in such way that they can not rotate with respect to each other, said thread bolt having an actuation sleeve;

a handle sleeve in which the proximal end of the tube has been fastened; and said actuation sleeve of said thread bolt can be pulled against said handle sleeve to produce a tractive force on said cable.

* * * * *